United States Patent [19]

Suga et al.

[11] Patent Number: 5,627,227

[45] Date of Patent: May 6, 1997

[54] ULTRAVIOLET ABSORBER AND COATING MATERIAL

[75] Inventors: Masanobu Suga; Tsuyoshi Asano; Nobuyuki Kuroda, all of Yokohama, Japan

[73] Assignee: Nippon Oil Co., Ltd., Tokyo, Japan

[21] Appl. No.: 609,558

[22] Filed: Mar. 1, 1996

[30] Foreign Application Priority Data

Mar. 13, 1995 [JP] Japan .................. 7-052992

[51] Int. Cl.$^6$ .................. C07D 249/00; C08K 5/3495
[52] U.S. Cl. .................. 524/91; 548/110
[58] Field of Search .................. 524/91; 548/110

[56] References Cited

U.S. PATENT DOCUMENTS

| | | | |
|---|---|---|---|
| 4,179,548 | 12/1979 | Schroete et al. | 524/91 |
| 4,316,033 | 2/1982 | Ching | 524/91 |
| 4,328,346 | 5/1982 | Chung et al. | 548/110 |
| 4,373,060 | 2/1983 | Ching | 548/100 |
| 4,504,628 | 3/1985 | Johnson | 524/91 |
| 4,923,914 | 5/1990 | Nohr et al. | 524/91 |
| 4,960,898 | 10/1990 | Sakuta et al. | 548/110 |
| 5,102,707 | 4/1992 | Canivenc et al. | 548/110 |
| 5,164,462 | 11/1992 | Yang | 548/110 |
| 5,244,947 | 9/1993 | Nohr et al. | 524/91 |
| 5,254,542 | 10/1993 | Sakuta et al. | 548/110 |
| 5,569,451 | 10/1996 | Richard et al. | 548/110 |

FOREIGN PATENT DOCUMENTS

| | | | |
|---|---|---|---|
| 0057160 | 8/1982 | European Pat. Off. | 548/110 |
| 282294 | 9/1988 | European Pat. Off. | |
| 63-43972 | 2/1988 | Japan . | |
| 2-243695 | 9/1990 | Japan . | |
| 4-132736 | 5/1992 | Japan . | |
| 6-88064 | 3/1994 | Japan . | |

*Primary Examiner*—Veronica P. Hoke
*Attorney, Agent, or Firm*—Darby & Darby

[57] ABSTRACT

An ultraviolet absorber contains as an effective component a compound represented by the formula:

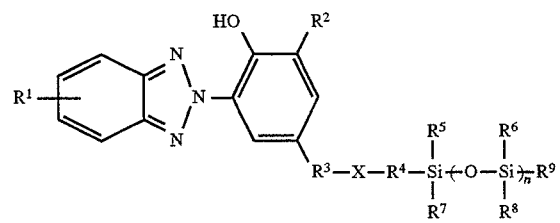

wherein $R^1$ denotes a hydrogen atom, a halogen atom or an alkyl group having 1 to 10 carbon atoms, $R^2$ denotes a hydrogen atom or an alkyl group having 1 to 10 carbon atoms, $R^3$ and $R^4$ denote the same or different groups and denote an alkylene group having 1 to 10 carbon atoms, $R^5$ to $R^9$ denote the same or different groups and denote an alkyl group having 1 to 10 carbon atoms, an alkoxy group having 1 to 10 carbon atoms, and an aryl group having 6 to 10 carbon atoms, a hydroxyl group or a hydrogen atom, X denotes an amido bond (CONH), a urethane bond (OCONH) or an ester bond (COO), and n is an integer of $n \geq 0$. A coating material contains the ultraviolet absorber.

19 Claims, 2 Drawing Sheets

ULTRAVIOLET ABSORBER AND COATING MATERIAL

BACKGROUND OF THE INVENTION

This invention relates to an ultraviolet absorber and a coating material containing the ultraviolet absorber.

It has hitherto been practiced to employ an organic ultraviolet absorber in conjunction with an acrylic resin for use as an ultraviolet protective coating. However, a problem is presented that, on prolonged use, leak out of the ultraviolet absorber or light deterioration of the polymer used as a basic material is produced to deteriorate the performance. For overcoming this drawback, attempts have been made in improving resin components or in employing an antioxidant in combination, as disclosed in Japanese Laid-open Patent Application No. 63-43972 (1988). Attempts have also been made in copolymerizing a basic polymer material with an organic ultraviolet absorber having methacryloyl groups for eliminating leak out (Japanese Laid-open Patent Application No. 6-88064 (1994)). However, since numerous ester bonds are contained in the main chain of the materials employed, Norrish type reaction is produced or the materials cannot be used under high temperature environments exceeding 200° C.

Also, a number of attempts have been made for introducing functional groups having silyl groups by hydrosilylation, as disclosed in Japanese Laid-open Patent Application No. 2-243695 (1990). However, difficulties are met in multiple application of silicone coatings employing silylated ultraviolet absorbers.

SUMMARY OF THE INVENTION

It is an object of the present invention to provide an ultraviolet absorber exhibiting superior ultraviolet absorbing performance, weatherability and thermal resistance, and capable of being stably held without leak out or the like even if co-used with the resin.

It is another object of the present invention to provide a coating material which is capable of being coated by multiple application and which gives a coating film exhibiting superior ultraviolet absorbing performance, weatherability and thermal resistance.

The above and other objects of the invention will become apparent from the following description.

According to the present invention, there is provided an ultraviolet absorber comprising as an effective component a compound represented by the formula (Hereinafter referred to as "compound A"):

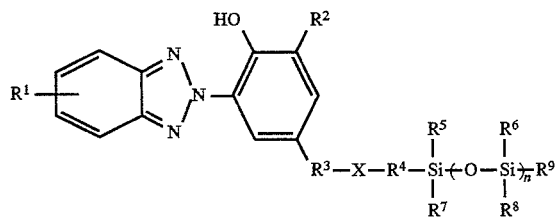

wherein $R^1$ denotes a hydrogen atom, a halogen atom or an alkyl group having 1 to 10 carbon atoms, $R^2$ denotes a hydrogen atom or an alkyl group having 1 to 10 carbon atoms, $R^3$ and $R^4$ denote the same or different groups and denote an alkylene group having 1 to 10 carbon atoms, $R^5$ to $R^9$ denote the same or different groups and denote an alkyl group having 1 to 10 carbon atoms, an alkoxy group having 1 to 10 carbon atoms, an aryl group having 6 to 10 carbon atoms, a hydroxyl group or a hydrogen atom, X denotes an amido bond (CONH), a urethane bond (OCONH) or an ester bond (COO), and n is an integer of $n \geq 0$.

According to the present invention, there is also provided a coating material containing the ultraviolet absorber.

PREFERRED EMBODIMENTS OF THE INVENTION

Figure 1:
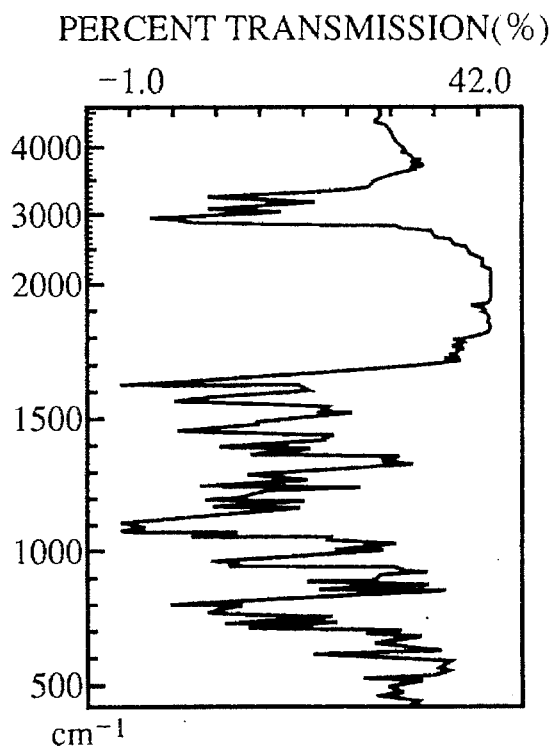
FIG. 1 is a graph showing infrared absorption spectrum for a compound (1) produced in Example 1.

The present invention will be explained in further detail.

The ultraviolet absorber of the present invention includes as an effective component the compound A represented by the aforementioned formula. $R^1$ in the formula denotes a hydrogen atom, a halogen atom or an alkyl group having 1 to 10, preferably 1 to 6 carbon atoms. The halogen atom includes a fluorine atom, a chlorine atom, a bromine atom and an iodine atom and preferably a chlorine or bromine atom. The alkyl group includes a methyl group, an ethyl group, a propyl group, an isopropyl group, a butyl group, a tert-butyl group and a cyclohexyl group. The position of substitution of $R^1$ may be 4-position or 5-position of triazole skeleton in the formula. The halogen atom and the alkyl group having 1 to 10 carbon atoms may usually be substituted at 5-position.

$R^2$ in the formula denotes a hydrogen atom or an alkyl group having 1 to 10, preferably 1 to 6 carbon atoms. The alkyl group may be enumerated by those mentioned as for $R^1$. $R^3$ and $R^4$ in the formula may be the same or different groups and denote an alkylene group having 1 to 10, preferably 1 to 3 carbon atoms. The alkylene group includes a methylene group, an ethylene group and a trimethylene group. $R^5$ to $R^9$ may be the same or different groups and denote an alkyl group having 1 to 10, preferably 1 to 6 carbon atoms, an alkoxy group having 1 to 10, preferably 1 to 6 carbon atoms, an aryl group having 6 to 10, preferably 6 to 8 carbon atoms, a hydroxyl group or a hydrogen atom. The alkyl group may be enumerated by those mentioned as for $R^1$. Examples of the alkoxy group include a methoxy group, an ethoxy group, an isopropoxy group, a propoxy group, a butoxy group and a tertiary butoxy group, while examples of the aryl group include a phenyl group and a xylyl group. If the number of carbon atoms as for $R^1$ to $R^9$ exceeds the pre-set upper limit, manufacture becomes difficult. n denotes an integer specified by $n \geq 0$ and preferably $0 \leq n \leq 20$.

The compound A represented by the above formula may be enumerated by 3-(5-methyl-2H-benzotriazole-2-yl)-5- methyl-4-hydroxy N-(2-(trimethoxy silyl)ethyl)-benzene propane amido, 3-(5-ethyl-2H-benzotriazole-2-yl)-4-hydroxy-N-(2-(1,1,3,3-tetramethyl disiloxy)ethyl)benzene propane amido, 3-(2H-benzotriazole-2-yl)-4-hydroxy benzene ethyl N-(3-(trimethoxy silyl)propyl) carbamate, 3-(5-chloro-2H-benzotriazole-2-yl)-4-hydroxy benzene propyl N-(2-nonaphenyl tetrasiloxy)ethyl) carbamate, 3-(5-chloro-2H-benzotriazole-2-yl)-5-(1,1-dimethylethyl)-4-hydroxy N-(3-triethoxysilyl) propyl)-benzene propane amido, 3-(5-chloro-2H-benzotriazole-2-yl)-5-(1,1-dimethylethyl)-4-hydroxy-N-(3-(triethoxysilyl)propyl)-benzene propane amido, 3-(5-chloro-2H-benzotriazole-2-yl)-5-(1,1-dimethylethyl)-4-hydroxy-N-(3-(henicosadimethyl decasiloxy)propyl)-benzene propane amido, 3-(2H-benzotriazole-2-yl)-4-hydroxy-N-(2-(1,1-dimethyl-trimethoxy disiloxy)ethyl)-benzene propane amido, 3-(triethoxysilyl)propyl 3-(5-chloro-2H-benzotriazole-2-yl 5-(1,1-dimethylethyl)4-hydroxy-benzene propanate, 3-(1,1,3,3,5,5,5-heptamethyl trisiloxy)propyl 3-(5-chloro-2H-benzotriazole-2-yl-5-(1,1-dimethylethyl)-4-hydroxy-benzene propanate and 3-(diethoxy methylsilyl)propyl 3-(2H-benzotriazole-2-yl)-5-(1,1-dimethylethyl)-4-hydroxy-benzene propanate.

In the above compound A a compound having an amido bond can be synthesized easily and has particularly superior thermal resistance. In particular, 3-(5-chloro-2H-benzotriazole-2-yl)-5-(1,1-dimethylethyl)-4-hydroxy-N-(3-(triethoxysilyl)propyl benzene propane amido, which is solid at room temperature, is preferably employed. On the other hand, a compound having a urethane bond gives physical properties superior in rigidity to the compound having the amido bond, while being low in crystallinity. In addition, if the compound is used in conjunction with a silicone-based coating, a hydrocarbon-based solvent such as toluene may be employed to facilitate handling. Such compound having the urethane bond may be enumerated by solid 3-(5-chloro-2H-benzotriazole-2-yl)-5-(1,1-dimethylethyl)-4-hydroxy benzene propyl N-(3-triethoxysilyl)propyl) carbamate. In addition, a compound having an ester bond exhibits physical properties superior in compatibility with resin to the aforementioned compound having the urethane bond. Such compound may be enumerated by liquid 3-(triethoxysilyl)propyl 3-(5-chloro-2H-benzotriazole-2-yl)-5-(1,1-dimethylethyl)-4-hydroxy-benzene propanate.

The compound A may be easily produced by, for example, a method consisting in reacting benzotriazoles with silanes, such as (i) a method of reacting benzotriazoles with silanes via an amido bond, (ii) a method of reacting benzotriazoles with silanes via a urethane bond, or (iii) a method of reacting benzotriazoles with silanes via an ester bond.

The above method (i) may be enumerated by a method of reacting carboxylic acids equivalent to a partial precursor of the compound A with amino silanes.

The carboxylic acids may be represented by the formula:

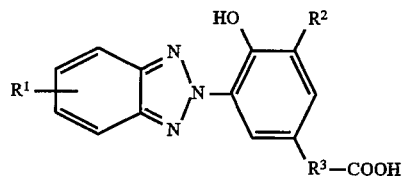

wherein $R^1$, $R^2$ and $R^3$ have the same meanings as those for the compound A.

Specifically, the carboxylic acids represented by the above formula may be enumerated by 3-(5-chloro-2H-benzotriazole-2-yl)-5-(1,1-dimethylethyl)-4-hydroxy-benzene propanoic acid, 3-(2H-benzotriazole-2-yl)-4-hydroxy-benzene ethanoic acid and 3-(5-methyl-2H-benzotriazole-2-yl)-5-(1-methylethyl)-4-hydroxy-benzene propanoic acid.

The aminosilanes may be represented by the formula:

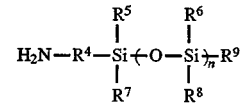

where $R^4$ to $R^9$ and n have the same meanings as those for the compound A.

Specifically, the aminosilanes shown by the above formula may be enumerated by 3-aminopropyl triethoxy silane, 3-aminopropyl diisopropyl ethoxy silane, 3-aminopropyl methyl diethoxy silane, 3-aminopropyl hexamethyl trisiloxane, 3-aminopropyl trimethoxy silane and 3-aminopropyl tris(methoxy ethoxy ethoxy)silane.

The condensation reaction between carboxylic acids and aminosilanes proceeds by removing moisture in a soluble solvent, such as toluene. For example, 3-(5-chloro-2H-benzotriazole-2-yl-5-(1,1-dimethylethyl)-4-hydroxy-N-(3-(triethoxysilyl)propyl) benzene propane amido may be formed by a method of hydrolyzing octyl 3-(5-chloro-2H-benzotriazole-2-yl)-5-(1,1-dimethylethyl)-4-hydroxy-benzene propanate, dissolving the resulting 3-(5-chloro-2H-benzotriazole-2-yl-5-(1,1-dimethylethyl)-4-hydroxy-benzene propanoic acid and an equimolar amount of 3-aminopropyl triethoxy silane in a soluble solvent and heating the resulting product to 90° to 100° C. for dehydration and condensation of the carboxylic acid group and the amino group.

After the condensation reaction, the product is preferably purified by, for example recrystallization. However, the product may be used without any inconvenience as the effective ingredient for the ultraviolet absorber, if it is substantially comprised of the above compound A, even granting that the product contains some amount of impurities. If a compound having an alkoxy group is used as a starting material for the aminosilanes, and if a condensation agent, such as dicyclocarbo diimido, is employed, or carboxylic acids are converted into esters having high reactivity, such as carbonate esters, before proceeding to the reaction, a product with high purity may be produced because of the absence of the dehydrating process.

The above method (ii) may be enumerated by a method of reacting alcohols equivalent to a partial precursor of the compound A with isocyanate silanes.

The alcohols may be represented by the formula:

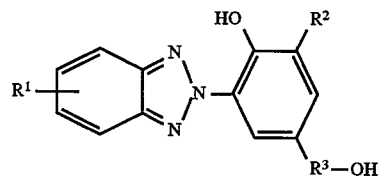

where $R^1$, $R^2$ and $R^3$ have the same meanings as those for the compound A.

Examples of the alcohols of the above formula include 3-(5-chloro-2H-benzotriazole-2-yl)-5-(1,1-dimethylethyl-4-hydroxy-benzene propanol, 3-(2H-benzotriazole-2-yl-4-hydroxy-benzene ethanol, and 3-(5-methyl-2H-benzotriazole-2-yl)-5-(1-methylethyl)-4-hydroxy-benzene propanol.

These alcohols may be synthesized or commercially available products. In addition, these alcohols may be produced by reducing commercially available benzotriazole based ultraviolet absorber having an ester group with lithium aluminum hydrides.

Examples of the isocyanate silanes include a compound represented by the formula:

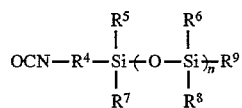

wherein $R^4$ and $R^9$ and n have the same meanings as those for the compound A. The isocyanate silanes may be enumerated by 3-isocyanate propyl triethoxy silane, 3-isocyanate propyl methoxy dimethyl silane and 2-isocyanate ethyl tetramethyl disiloxane.

The addition reaction between alcohols and diisocyanate silanes proceeds in a soluble solvent, such as tetrahydrofuran in the presence of a catalyst such as dibutyltin dilaurate. For example, 3-(5-chloro-2H-benzotriazole-2-yl-5-(1,1-dimethylethyl)-4-hydroxy benzene propyl N-(3-(triethoxysilyl)propyl) carbamate may be formed by reacting 3-(5-chloro-2H-benzotriazole-2-yl)-5-(1,1-dimethylethyl)- 4-hydroxy benzene propanol and 3-isocyanate propyl triethoxy silane at 30° to 60° C. in a soluble solvent such as tetrahydrofuran with addition of dibutyltin dilaurate.

The method (iii) may be enumerated by a method of addition reaction of esters equivalent to a partial precursor of the compound A with silanes containing hydrosilyl groups.

Examples of the above esters may be represented by the formula:

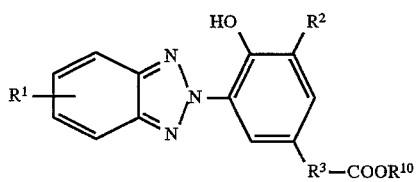

wherein $R^1$, $R^2$ and $R^3$ have the same meanings as those for the compound A and $R^{10}$ is a C1 to C10 hydrocarbon group containing an unsaturated double bond and being capable of being addition-reacted to the same compound as $R^4$ of the compound A.

The esters may be enumerated by 2-propenyl 3-(5-chloro-2H-benzotriazole-2-yl-5-(1,1-dimethylethyl)-4-hydroxy-benzene propanate, vinyl 3-(2H-benzotriazole-2-yl)-4-hydroxy-benzene ethanate and 3-methyl-3-butenyl 3-(5-methyl-2H-benzotriazole-2-yl)-5-(1-methylethyl)-4-hydroxy-benzene propanate.

The silanes may be represented by the formula:

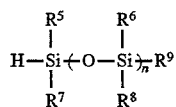

where $R^5$ to $R^9$ and n have the same meanings as those for the compound A.

Examples of the silanes include triethoxysilane, diisopropyl ethoxy silane, methyldiethoxy silane, 1,1,1-3,3-5,5-heptamethyl trisiloxane and polymethyl siloxane.

The above-mentioned addition reaction between the esters and the hydrosilyl group-containing silanes proceeds by employing a catalyst, such as chloroplatinic acid in a soluble solvent such as toluene or tetrahydrofuran. For example, 3-(triethoxysilyl)propyl 3-(5-chloro-2H-benzotriazole-2-yl)-5-(1,1-dimethylethyl)-4-hydroxy-benzene propanate may be formed by ester-exchanging octyl 3-(5-chloro-2H-benzotriazole-2-yl)-5-(1,1-dimethylethyl)-4-hydroxy-benzene propanate in allyl alcohol, dissolving the resulting allyl 3-(5-chloro-2H-benzotriazole-2-yl)-5-(1,1-dimethylethyl)-4-hydroxy-benzene propanate in tetrahydrofuran, adding a platinum siloxane complex to the resulting mass, adding an equimolar amount of triethoxy silane dropwise to the resulting mass and agitating the resulting mixture at room temperature.

After the condensation reaction, the product is preferably passed through a column for purification. However, the product may be used without any inconvenience as the effective component for the ultraviolet absorber, if it is substantially comprised of the above compound A, even granting that the product contains some amount of impurities.

The ultraviolet absorber according to the present invention contains the compound A as an effective component, and may be employed as a coating material as later explained. The compound A itself has the ultraviolet absorbing performance and may be employed as, for example a mixture with a resin or a solvent. If the above compound A is contained in an amount of not less than 0.1 wt %, preferably in an amount from 0.1 to 90 wt % and more preferably in an amount from 0.5 to 70 wt %, the desired ultraviolet absorbing performance may be achieved. With a larger value of n in the compound A, the compound A may be present partially on the resin surface, if the resin is used in combination, so that desired effects may be achieved even if the compound A is employed in a minimum amount.

The coating material according to the present invention contains the above-mentioned ultraviolet absorber. The coating material may be employed as a coating or a hard coating material. The substrate material employed may be glass, metal plate or wooden plate, whichever is desired.

If the coating material is used as a coating, a coating film-forming resin is contained in addition to the ultraviolet absorber. Although there is no particular limitation to the coating film-forming resins employed, these may be enumerated by a variety of polymers, such as silicone resin, acrylic resins, acrylic melamine resin, polyolefin, polystyrene, polyacrylonitrile, polycarbonate, polyether sulfone, polyimide, polyamide or polyvinyl chloride, and copolymers, polymer blends or grafted polymers of these resins. Most preferred is a resin material containing silicone resins. In this case, however, the compound A preferably contains a group reactable with the silicone resin, such as pure silicone varnish, specifically an alkoxy group or a silanol group. If the silicone varnish based coating or a silicone resin based coating material, for example is employed, the ultraviolet absorber reacts with the resin such that leak out does not occur and an optimum ultraviolet absorbing performance may be maintained even if the coating material is employed for prolonged time.

If the coating material is used as a coating, the amount of the compound A as an effective component of the ultraviolet absorber may be optionally set in a range usually from 5 to 90 wt % depending upon the substrate to be applied. The compound A is preferably employed in a higher concentration of not less than 20 wt % in view of superior compatibility proper to the ultraviolet absorber of the present invention.

If the compound A is contained in such a high concentration, the critical surface tension of the coating film is increased such that overcoating becomes feasible with the use of solvents, such as toluene or isopropanol. If 3-(5-chloro-2H-benzotriazole-2-yl)-5-(1,1-dimethylethyl)-4-hydroxy-N-(3-(triethoxysilyl)propyl)-benzene propane amido is contained in an amount on the order of 50 wt % in a silicone coating film, and when a water-isopropanol mixed solvent with a mixing ratio of 1:1 is used, colloidal silica which is highly water-repellent and hence cannot be coated without difficulties, may be employed as an overcoating.

For further suppressing deterioration in performance, antioxidants, quenchers or radical scavengers may be contained in the coating. For coating, solvents such as toluene or isopropanol may also be employed. Although the coating may be applied to have desired film thickness without any particular limitations, it can usually be coated in a range from 0.5 to 50 μm. If the film thickness is less than 0.5 μm, sufficient ultraviolet shielding capacity cannot be achieved, whereas if it exceeds 50 μm, it becomes occasionally difficult to apply the coating without forming cracks.

There is no particular limitation to the coating method which may be suitably selected from known methods. For example, spin coating, spray coating, cast coating, blade coating or dip coating may be selected depending on usage and application.

For curing the coating film, acids, such as hydrochloric acid, sulfuric acid or acetic acid, bases, such as potassium hydroxide, triethylamine or aniline or organometal compounds, such as dibutyltin dilaurate or titanium tetraisopropoxide, are pre-mixed as a catalyst in a coating, and the resulting mass is cured at room temperature to 250° C. Alternatively, the coating not containing the catalyst may be heated at room temperature to 350° C. for curing. The mixing ratio of the catalyst is preferably 0.1 to 5.0 wt % based on the total weight of the ultraviolet absorber and the coating film-forming resin.

The coating material of the present invention may also be obtained by dissolving the ultraviolet absorber in a solvent, such as toluene, thinner, dimehyl formamide or cyclohexanone. The compound A as an effective component of the ultraviolet absorber preferably contains an alkoxy silyl group. The content of the compound A preferably is 0.1 to 90 wt %.

There is no particular limitation to the coating film thickness of the coating material containing the ultraviolet absorber dissolved in a solvent. The coating film thickness usually of 0.2 to 20 μm is preferred. If the coating film thickness of less than 0.2 μm, sufficient ultraviolet absorbing performance occasionally cannot be achieved, whereas if the film thickness exceeds 20 μm, it becomes occasionally difficult to apply the coating material without forming cracks. There is no particular limitation to the coating methods. For example spin coating, spray coating, cast coating, blade coating or dip coating may be selected depending on usage and application.

Since the ultraviolet absorber contains the particular compound A, it exhibits superior ultraviolet absorbing performance. If the ultraviolet absorber is co-used with the resin, the ultraviolet absorber may be held stably without leak out by proper selection of the resin employed. In particular, if the coating material of the present invention is co-used with the silicone resin, a coating film superior in weatherability and thermal resistance may be obtained.

EXAMPLES OF THE INVENTION

The present invention is explained in further detail with reference to the following merely illustrative Examples.

Example 1

2.0 g (7.8 mmol) of 3-(2H-benzotriazole-2-yl)4-hydroxy benzene ethanol manufactured and sold by JOHOKU CHEMICAL CO., LTK. under the trade name of "JF-269", were dissolved in 20 ml of tetrahydrofuran. To the resulting mixture were added 2.13 g (8.2 mmols) of 3-isocyanate propyl triethoxy silane and 20 μl of dibutyltin dilaurate and reaction was carried out at 60° C. for 10 minutes. After removing the solvent, 3-(2H-benzotriazole-2-yl)-4-hydroxy benzene ethyl N-(3-(triethoxysilyl)propyl) carbamate, referred to hereinafter as a compound (1), shown by the formula:

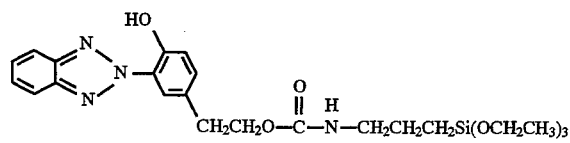

was produced by recrystallization from ethanol. The compound (1) having a melting point of 107° C. was produced with a yield of 90%. FIG. 1 shows the infrared absorption spectrum of the produced compound (1).

Figure 2:
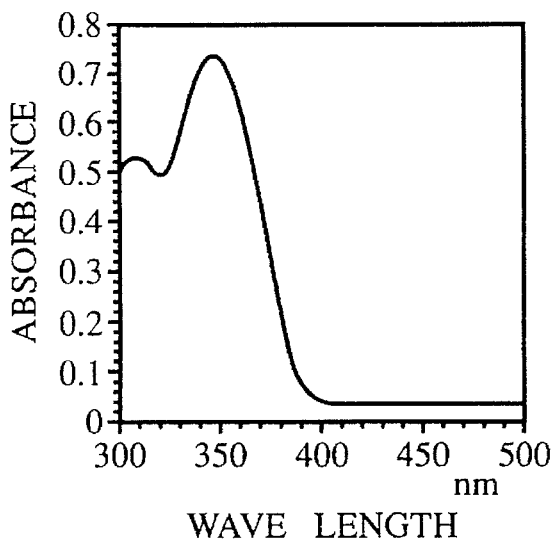
FIG. 2 is a graph showing ultraviolet absorption spectrum in Example 1.

On the other hand, 10 mg of the compound (1) were dissolved in 50 ml of chloroform, and measurement was made of the ultraviolet absorption spectrum using a quartz cell having a light path length of 1 mm. The results are shown in FIG. 2 from which it is seen that the compound (1) exhibits sufficient absorption in an ultraviolet range.

Example 2

2.87 g (0.076 mol) of aluminum lithium hydride were suspended in 50 ml of tetrahydrofuran and cooled with ice. To this suspension was added dropwise a solution obtained by dissolving 28.7 g (0.059 mol) of octyl 3-(5-chloro-2H-benzotriazole-2-yl)-5-(1,1-dimethyl)-4-hydroxy-benzene propanate manufactured by CIBA GEIGY INC. under the trade name of "TINUVIN 109" in 100 ml of tetrahydrofuran, and the resulting mass was agitated at room temperature for one hour. The resulting reaction solution was gradually added dropwise to 200 ml of a 2N aqueous solution of hydrochloric acid under ice cooling. The mixed liquid was extracted with methylene chloride to give an organic layer, which was dried over magnesium sulfate and the solvent was distilled off. The produced solid was recrystallized from ethanol to give 3-(5-chloro-2H-benzotriazole-2-yl)-5-(1,1-dimethylethyl)-4-hydroxy-benzene propanol, referred to hereinafter as a precursor (1).

Figure 3:
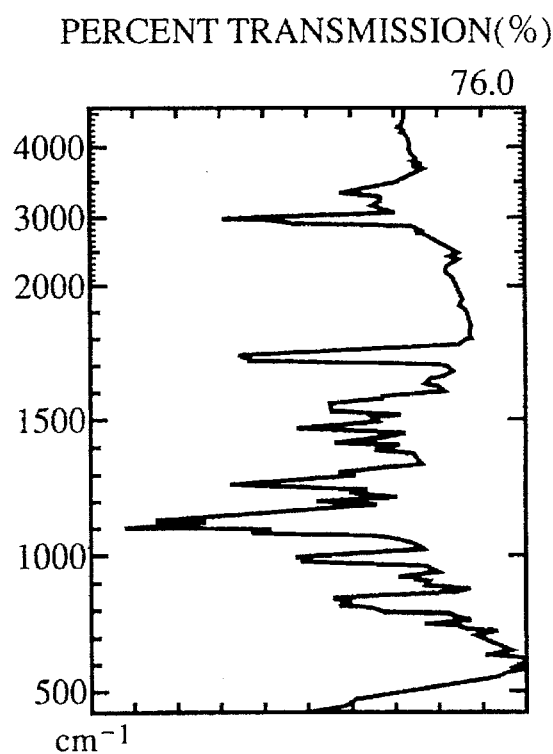
FIG. 3 is a graph showing infrared absorption spectrum for a compound (2) produced in Example 2.

9.9 g (0.027 mol) of the produced precursor (1) were dissolved in 20 ml of a tetrahydrofuran solution. To the resulting mass were added 7.9 g (0.032 mol) of 3-isocyanate propyl triethoxy silane and 20 μl of dibutyltin dilaurate and the resulting mixture was reacted at 60° C. for one hour. After removing tetrahydrofuran, 3-(5-chloro-2H-benzotriazole-2-yl)5-(1,1-dimethylethyl)-4-hydroxy benzene propyl N-(3-(triethoxysilyl)propyl) carbamate shown by formula:

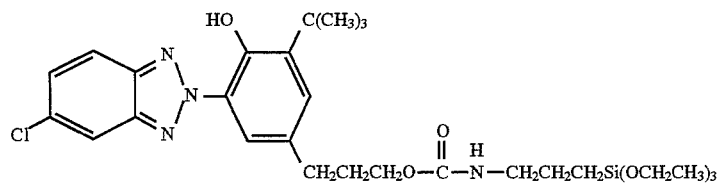

having a melting point of 90° C., referred to hereinafter as a compound (2), was produced with a yield of 85%. FIG. 3 shows infrared absorption spectrum of the compound (2).

Figure 4:
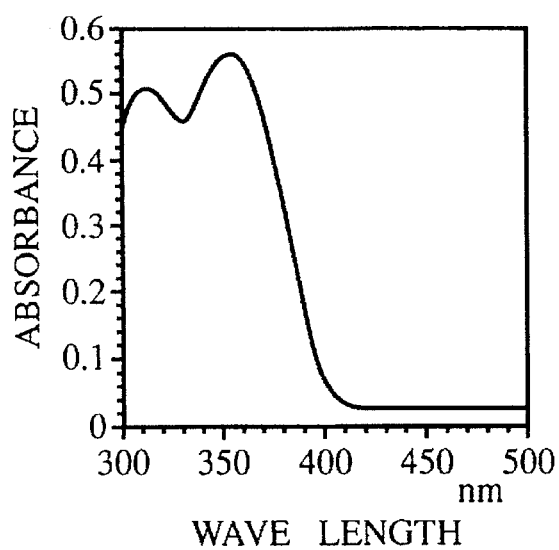
FIG. 4 is a graph showing ultraviolet absorption spectrum in Example 2.

Measurement was made of ultraviolet absorption spectrum of the compound (2), as in Example 1. The results are shown in FIG. 4, from which it is seen that the compound (2) shows sufficient absorption in the ultraviolet range.

EXAMPLE 3

5.1 g (0.01 mol) of octyl 3-(5-chloro-2H-benzotriazole-2-yl)-5-(1,1-dimethylethyl)-4-hydroxy-benzene propanate manufactured by CIBA GEIGY INC. under the trade name of "TINUVIN 109", and 1.5 g (0.02 mol) of allylamine, were dissolved in 20 ml of benzene. To the resulting solution were added 1.36 g (0.025 mol) of NaOCH₃ and heated at 80° C. for two hours. After cooling, the reaction solution was poured into a 10 wt % aqueous solution of HCl and extracted with chloroform. An organic layer was dried over magnesium sulfate and filtered to distill off the solvent to produce a while solid substance. This substance was recrystallized from ethanol to give N-allyl-3-(5-chloro-2H-benzotriazole-2-yl)-5-(1,1-dimethylethyl)-4-hydroxy-benzene propane amido, referred to hereinafter as a precursor (2).

1.95 g (0.005 mol) of the produced precursor (2) and 0.78 g (0.005 mol) of triethoxysilane were dissolved in 10 ml of tetrahydrofuran. To the resulting solution heated to 60° C. was added 0.1 ml of a platinum-siloxane complex. After heating for two hours, the solvent was distilled off, and the resulting mass was vacuum-dried to give a pale yellow solid substance. This substance was recrystallized from ethanol to give 3-(5-chloro-2H-benzotriazole-2-yl)-5-(1,1-dimethylethyl)4-hydroxy-N-(3-(triethoxysilyl)propyl) benzene propane amido (melting point: 139° to 140° C.), referred to hereinafter as a compound (3), having the formula:

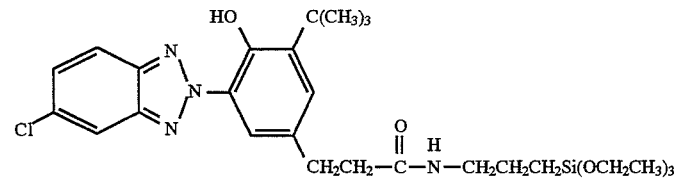

with a yield of 90%.

Measurements were made of ultraviolet absorption spectrum as in Example 1. Sufficient absorption was achieved in the ultraviolet region.

Example 4

225 g (0.46 mol) of octyl 3-(5-chloro-2H-benzotriazole-2-yl)-5-(1,1-dimethylethyl)-4-hydroxy-benzene propanate manufactured by CIBA GEIGY INC. under the trade name of "TINUVIN 109" were dissolved in 700 ml of acetone. To the resulting solution were added 600 ml of a 2N aqueous solution of sodium hydroxide followed by agitation at room temperature for 24 hours. Then, 650 ml of a 2N aqueous solution of hydrochloric acid was added to give an acidic solution and an insolubilized product was filtered off and rinsed with distilled water until the filtrate turned neutral. After vacuum-drying the product, it was recrystallized from toluene to give 3-(5-chloro-2H-benzotriazol-2-yl)-5-(1,1-dimethylethyl)-4-hydroxy benzene propanoic acid, referred to hereinafter as a precursor (3).

3.88 g (0.01 mol) of the produced precursor (3) were dissolved in 100 ml of acetone to give a solution, to which 1.78 g (0.018 mol) of triethylamine was added dropwise. After the end of the dropwise addition, the resulting mass was agitated for a while and cooled to 0° C., to which 1.14 g (0.01 mol) of ethyl chlorocarbonate was slowly added dropwise. After the end of the dropwise addition, the solution was agitated at the same temperature for 30 minutes. The produced precipitate was filtered. The resulting filtrate was cooled to 0° C. and 2.3 g (0.01 mol) of 3-amino propyl triethoxysilane was added thereto dropwise. After the end of the dropwise addition, the resulting mass was agitated at room temperature for 30 minutes and the reaction solution was cooled to give a precipitate, which was then filtered, rinsed with cooled acetone and dried to give the compound (3)having a melting point of 139° to 140° C.

Measurements were made of ultraviolet absorption spectrum as in Example 1. Sufficient absorption was achieved in the ultraviolet region.

Example 5

6.47 g (0.017 mol) of the precursor (3) prepared in Example 4 were dissolved in 100 ml of toluene and admixed with 3.91 g (0.017 mol) of 3-aminopropyl triethoxy silane. After heating the resulting mixture at 110° C. for three hours, toluene was distilled off, and the resulting solid substance was dried to give the compound (3) with a yield of 80%.

100 g of the compound (3) were dissolved in 300 ml of N,N-dimethyl formamide and admixed with 222 g of a silicone varnish manufactured by OKITSUMO CO. under the trade name of "XO-7931-CLEAR". The resulting mixture was further admixed with 10 ml of water, 1 ml of acetic acid and 0.1 ml of di-n-butyltin dilaurate and the resulting mixture was agitated under heating at 60° C. for two hours to give a coating liquid, which was then applied by a 10 mil applicator on a glass substrate and heated at 200° C. for 20 minutes to produce a glass substrata having a an ultraviolet absorption layer with a thickness of approximately 15 μm.

On the ultraviolet absorption layer was spray-coated a silicone resin manufactured by NIPPON UNICAR COMPANY LTD. under the trade name of "APZ-6615" and the resulting product was dried at 100° C. for 20 minutes to provide a protective layer having a thickness of approximately 2 μm.

Figure 5:
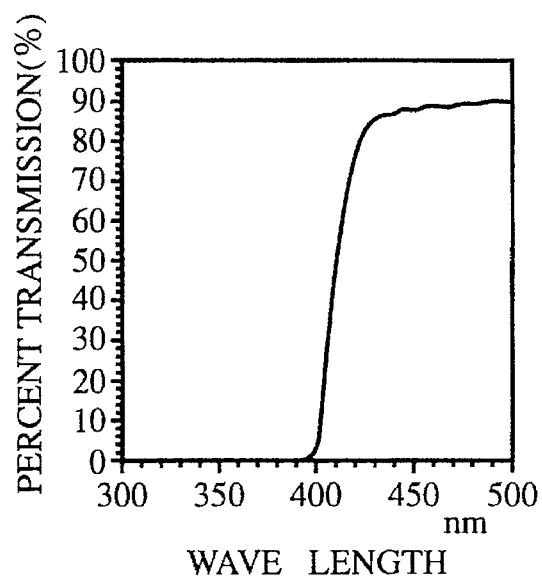
FIG. 5 is a graph showing ultraviolet absorption spectrum of a glass substrate having an ultraviolet absorbing layer in Example 5.

FIG. 5 shows ultraviolet absorption spectrum of the glass substrate. It is seen from this figure that the glass substrate produced is capable of completely shielding the ultraviolet rays.

Example 6

220 g (0.45 mol) of octyl 3-(5-chloro-2H-benzotriazole-2-yl)-5-(1,1-dimethylethyl)-4-hydroxy-benzene propanate manufactured by CIBA GEIGY INC. under the trade name of "TINUVIN 109" were dissolved in 500 ml of allyl alcohol, and was admixed with 5 ml of concentrated sulfuric acid. The resulting solution was refluxed for five hours. After cooling, a precipitated product was filtered off. The resulting solid substance was dissolved in 300 ml of methylene chloride, washed with a saturated aqueous solution of NaHCO₃ and dried over magnesium sulfate. After filtration, the solvent was distilled off and the resulting solid substance was recrystallized from hexane to produce allyl 3-(5-chloro-2H-benzotriazole-2-yl)-5-(1,1-dimethylethyl)-4-hydroxy-benzene propanate, referred to hereinafter as a precursor (4) at a yield of 90%.

Figure 6:
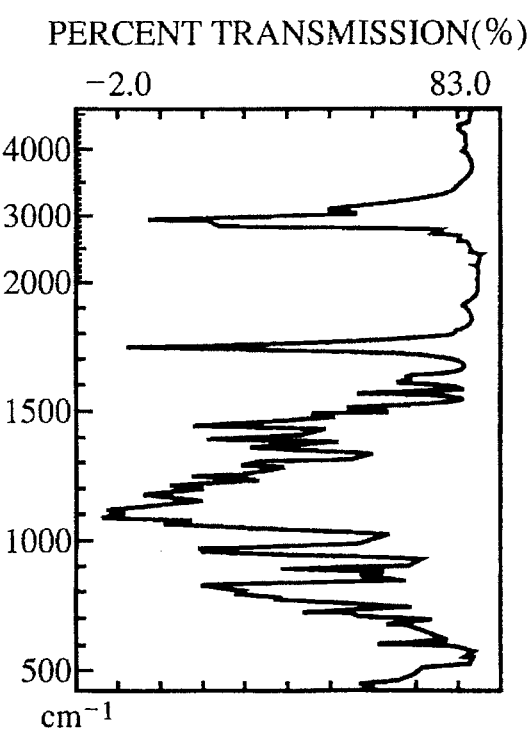
FIG. 6 is a graph showing infrared absorption spectrum for a compound (4) produced in Example 6.

69.13 g (0.167 mol) of the precursor (4) was dissolved in 300 ml of tetrahydrofuran and admixed with 0.6 ml of platinum-siloxane complex. To the resulting mixture were added 30.6 g (0.186 mol) of triethoxy silane dropwise. After agitation for six hours, the solvent was distilled off and the resulting mass was vacuum-dried to give a pale yellowish liquid, which was passed through a FLORISIL column along with 500 ml of hexane/ether with a volume ratio of 3:1 to give a liquid compound 3-(triethoxysilyl)propyl 3-(5-chloro-2H-benzotriazole-2-yl)-5-(1,1-dimethylethyl)4-hydroxy-benzene propanate, having the formula:

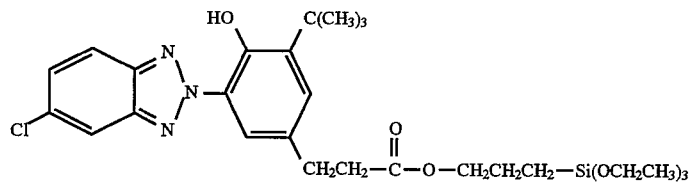

referred to hereinafter as a compound (4), with a yield of 90%. FIG. 6 shows the infrared absorption spectrum of the compound (4).

Figure 7:
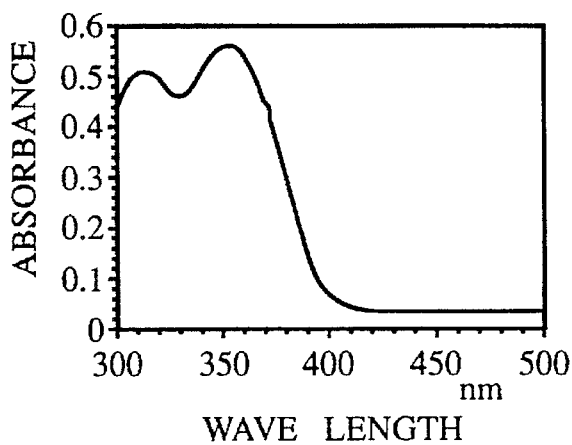
FIG. 7 is a graph showing ultraviolet absorption spectrum in Example 6.

The ultraviolet absorption spectrum of the compound (4) was measured as in Example 1. The results are shown in FIG. 7, from which it is seen that the compound (4) exhibits sufficient absorption in the ultraviolet range.

Example 7

5.0 g (0.012 mol) of the precursor (4) was dissolved in 50 ml of tetrahydrofuran and admixed with 0.4 ml of a platinum-siloxane complex. To the resulting solution were added dropwise 4.0 g (0.018 mol) of 1,1,1,3,3,5,5-heptamethyl trisiloxane. After agitation for six hours, the solvent was distilled off and the resulting mass was vacuum-dried to give a pale yellowish liquid, which was passed through a FLORISIL column along with 500 ml of hexane/ether with a volume ratio of 3:1 to give 1-(1,1,3,3,5,5,5-heptamethyl trisiloxy)propyl 3-(5-chloro-2H-benzotriazole-2-yl)-5-(1,1-dimethylethyl)-4-hydroxy-benzene propanate having the formula:

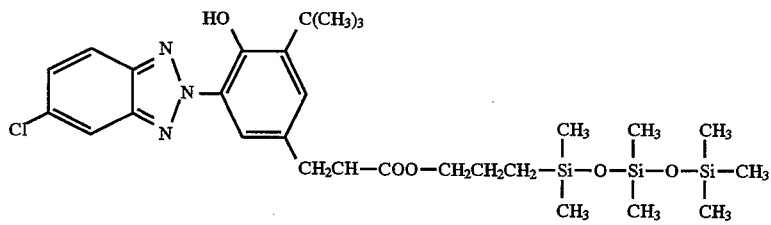

referred to hereinafter as a compound (5) at a yield of 90%.

Figure 8:
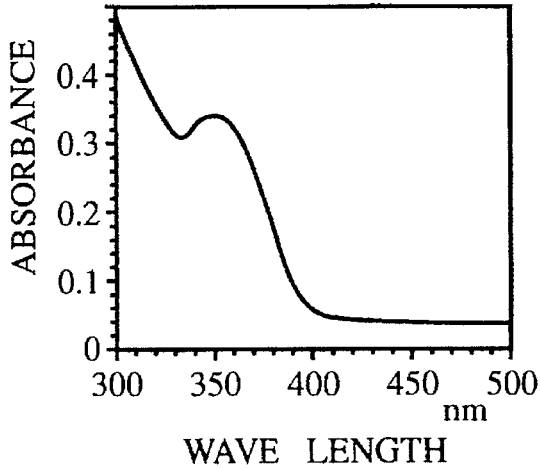
FIG. 8 is a graph showing ultraviolet absorption spectrum in Example 7.

15 mg of the compound (5) was dissolved in 50 ml of chloroform and the ultraviolet absorption spectrum was measured in the same way as in Example 1. The results are shown in FIG. 8, from which it is seen that the compound (5) exhibits sufficient absorption in the ultraviolet range.

Although the present invention has been described with reference to the preferred examples, it should be understood that various modifications and variations can be easily made by those skilled in the art without departing from the spirit of the invention. Accordingly, the foregoing disclosure should be interpreted as illustrative only and is not to be interpreted in a limiting sense. The present invention is limited only by the scope of the following claims.

What is claimed is:

1. An ultraviolet absorber comprising as an effective component a compound represented by the formula:

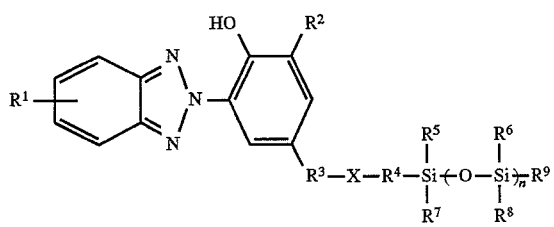

wherein $R^1$ denotes a hydrogen atom, a halogen atom or an alkyl group having 1 to 10 carbon atoms, $R^2$ denotes a hydrogen atom or an alkyl group having 1 to 10 carbon atoms, $R^3$ and $R^4$ denote the same or different groups and denote an alkylene group having 1 to 10 carbon atoms, $R^5$ to $R^9$ denote the same or different groups and denote an alkyl group having 1 to 10 carbon atoms, an alkoxy group having 1 to 10 carbon atoms, and an aryl group having 6 to 10 carbon atoms, a hydroxyl group or a hydrogen atom, X denotes an amido bond (CONH), a urethane bond (OCONH) or an ester bond (COO), and n is an integer of $n \geq 0$.

2. The ultraviolet absorber according to claim 1 wherein each of $R^1$ and $R^2$ is selected from the group consisting of a methyl group, an ethyl group, a propyl group, an isopropyl group, a butyl group, a tertiary butyl group and a cyclohexyl group.

3. The ultraviolet absorber according to claim 1 wherein said halogen atom of $R^1$ is a chlorine atom or a bromine atom.

4. The ultraviolet absorber according to claim 1 wherein each of $R^3$ and $R^4$ is selected from the group consisting of a methylene group, an ethylene group and a trimethylene group.

5. The ultraviolet absorber according to claim 1 wherein each of $R^5$ to $R^9$ is selected from the group consisting of a methyl group, an ethyl group, a propyl group, an isopropyl group, a butyl group, a tertiary butyl group, a cyclohexyl group, a methoxy group, an ethoxy group, an isopropoxy group, a propoxy group, a butoxy group, a tertiary butoxy group, a phenyl group and a xylyl group.

6. The ultraviolet absorber according to claim 1 wherein n is $0 \leq n \leq 20$.

7. The ultraviolet absorber according to claim 1 wherein said compound is selected from the group consisting of 3-(5-methyl-2H-benzotriazole-2-yl)-5-methyl-4-hydroxy-N-(2-(trimethoxy silyl)ethyl)-benzene propane amido, 3-(5-ethyl-2H-benzotriazole-2-yl)-4-hydroxy-N-(2-(1,1,3,3-tetramethyl disiloxy)ethyl)benzene propane amido, 3-(2H-benzotriazole-2-yl)-4-hydroxy benzene ethyl N-(3-(trimethoxy silyl)propyl) carbamate, 3-(5-chloro-2H-benzotriazole-2-yl)-4-hydroxy benzene propyl N-(2-(nonaphenyl tetrasiloxy)ethyl) carbamate, 3-(5-chloro-2H-benzotriazole-2-yl)-5-(1,1-dimethylethyl)-4-hydroxy-N-(3-(triethoxysilyl)propyl)-benzene propane amido, 3-(5-chloro-2H-benzotriazole-2-yl)-5-(1,1-dimethylethyl)-4-hydroxy-N-(3-(triethoxysilyl)propyl)-benzene propane amido, 3-(5-chloro-2H-benzotriazole-2-yl)-5-(1,1-dimethylethyl)-4-hydroxy-N-(3-(henicosadimethyl decasiloxy)propyl)-benzene propane amido, 3-(2H-benzotriazole-2-yl)-4-hydroxy-N-(2-(1,1-dimethyltrimethoxy disiloxy)ethyl)-benzene propane amido, 3-(triethoxysilyl)propyl 3-(5-chloro-2H-benzotriazole-2-yl)-5-(1,1-dimethylethyl) 4-hydroxy-benzene propanate, 3-(1,1,3,3,5,5-heptamethyl trisiloxy)propyl 3-(5-chloro-2H-benzotriazole-2-yl)-5-(1,1-dimethylethyl)-4-hydroxy-benzene propanate and 3-(diethoxy methylsilyl)propyl 3-(2H-benzotriazole-2-yl)-5-(1,1-dimethylethyl)-4-hydroxy-benzene propanate.

8. The ultraviolet absorber according to claim 1 containing not less than 0.1 wt % of the compound represented by said formula.

9. The ultraviolet absorber according to claim 8 containing 0.1 to 90 wt % of the compound represented by said formula.

10. A coating material comprising the ultraviolet absorber of claim 1 containing the compound represented by said formula.

11. The coating material according to claim 10 further comprising a coating film-forming resin.

12. The coating material according to claim 11 wherein said coating film-forming resin is a polymer selected from the group consisting of a silicone resin, an acrylic resin, an acrylic melamine resin, polyolefin, polystyrene, polyacrylonitrile, polycarbonate, polyether sulfone, polyimide, polyamide, polyvinyl chloride and mixtures thereof.

13. The coating material according to claim 12 wherein said polymer is selected from the group consisting of a copolymer, a blend, and a grafted polymer of said polymer and mixtures thereof.

14. The coating material according to claim 10 comprising 5 to 90 wt % of the compound represented by said formula.

15. The coating material according to claim 11 further comprising a curing catalyst.

16. The coating material according to claim 15 wherein said catalyst is selected from the group consisting of hydrochloric acid, sulfuric acid, acetic acid, potassium hydroxide, triethylamine, aniline, dibutyltin dilaurate and titanium tetraisopropoxide.

17. The coating material according to claim 10 comprising said ultraviolet absorber dissolved in a solvent and containing the compound represented by said formula.

18. The coating material according to claim 17 wherein said solvent is selected from the group consisting of toluene, thinner, dimethyl formamide, cyclohexanone and mixtures thereof.

19. The coating material according to claim 17 containing 0.1 to 90 wt % of the compound represented by said formula.

* * * * *